(12) United States Patent
VanGompel et al.

(10) Patent No.: US 6,336,922 B1
(45) Date of Patent: *Jan. 8, 2002

(54) ABSORBENT ARTICLE HAVING A FIT PANEL

(75) Inventors: Paul Theodore VanGompel, Hortonville; Timothy James Blenke; Nancy Ellen Dawson, both of Neenah; Yung Hsiang Huang; Carl Gerard Rippl, both of Appleton; Barbara Oakley Sauer, Fremont; Georgia Lynn Zehner, Larsen, all of WI (US)

(73) Assignee: Kimberly-Clark Worldwide, Inc., Neenah, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/739,231

(22) Filed: Oct. 28, 1996

Related U.S. Application Data

(60) Provisional application No. 60/020,302, filed on Jun. 19, 1996.

(51) Int. Cl.[7] .................................................. A61F 13/15
(52) U.S. Cl. .............................. 604/385.3; 604/385.29; 604/392
(58) Field of Search ............................... 604/358, 385.1, 604/385.2, 390–392, 386–387, 397, 398, 385.23–385.3

(56) References Cited

U.S. PATENT DOCUMENTS

| 3,658,064 A | 4/1972 | Pociluyko | |
| 4,450,026 A | * 5/1984 | Pleniak et al. | 604/385.2 |
| 4,490,148 A | 12/1984 | Beckestrom | |
| 4,662,877 A | 5/1987 | Williams | |
| 4,663,220 A | 5/1987 | Wisneski et al. | 428/221 |

(List continued on next page.)

FOREIGN PATENT DOCUMENTS

| AU | 669855 | 3/1993 |
| EP | 0217032 | 4/1987 |
| EP | 0 404 648 | 12/1990 |
| EP | 0692230 | 1/1996 |
| FR | 2 680 316 | 2/1993 |
| GB | 2 291 783 | 2/1996 |
| WO | 93/03698 | 3/1993 |
| WO | 95/14453 | 6/1995 |
| WO | 95/22951 | 8/1995 |
| WO | 95/32697 | 12/1995 |
| WO | 95/32698 | 12/1995 |
| WO | 96/03951 | 2/1996 |
| ZA | 92/6027 | 8/1992 |

* cited by examiner

Primary Examiner—John G. Weiss
Assistant Examiner—K. M. Reichle
(74) Attorney, Agent, or Firm—Jeffrey B. Curtin; Alyssa A. Dudkowski

(57) ABSTRACT

An absorbent article includes at least one fit panel which is located in one of the waist sections of the absorbent article adjacent an end edge of the absorbent article. The fit panel extends laterally beyond both of the side edges of an absorbent chassis of the absorbent article. The fit panel may include a center bridge panel and a pair of laterally opposed side panels which are connected to opposed lateral edges of the bridge panel. Desirably, the bridge panel and side panels provide individual zones of elasticity across the width of the fit panel which have different elastic properties.

48 Claims, 4 Drawing Sheets

U.S. PATENT DOCUMENTS

| | | |
|---|---|---|
| 4,681,580 A | 7/1987 | Reising et al. |
| 4,701,171 A | 10/1987 | Boland et al. |
| 4,704,116 A | 11/1987 | Enloe |
| 4,738,677 A | 4/1988 | Foreman |
| 4,743,246 A | 5/1988 | Lawson |
| 4,753,646 A | 6/1988 | Enloe |
| 4,798,603 A | 1/1989 | Meyer et al. ................ 604/378 |
| 4,816,025 A | 3/1989 | Foreman .................. 604/385.2 |
| 4,846,823 A | 7/1989 | Enloe ..................... 604/385.2 |
| 4,846,825 A | 7/1989 | Enloe et al. ............. 604/385.1 |
| 4,892,536 A | 1/1990 | DesMarais et al. ...... 604/385.2 |
| 4,895,568 A | 1/1990 | Enloe ..................... 604/385.2 |
| 4,938,753 A | 7/1990 | Van Gompel et al. ... 604/385.2 |
| 4,990,147 A | 2/1991 | Freeland ................. 604/385.2 |
| 4,998,929 A | 3/1991 | Bjorksund et al. ....... 604/385.2 |
| 5,019,066 A | 5/1991 | Freeland et al. ......... 604/385.2 |
| 5,026,364 A | 6/1991 | Robertson ................ 604/385.1 |
| 5,106,385 A | 4/1992 | Allen et al. ................. 604/391 |
| 5,151,092 A | 9/1992 | Buell et al. ............... 604/385.2 |
| 5,176,668 A | 1/1993 | Bernardin .................... 604/368 |
| 5,176,672 A | 1/1993 | Bruemmer et al. ...... 604/385.1 |
| 5,192,606 A | 3/1993 | Proxmire et al. ........... 428/284 |
| 5,196,000 A | 3/1993 | Clear et al. ............... 604/385.2 |
| 5,207,663 A | 5/1993 | McQueen ................ 604/385.1 |
| 5,221,274 A | 6/1993 | Buell et al. ............... 604/385.2 |
| 5,226,992 A | 7/1993 | Morman .................... 156/62.4 |
| 5,254,111 A | 10/1993 | Cancio et al. ........... 604/385.1 |
| 5,269,775 A | 12/1993 | Freeland et al. ......... 604/385.2 |
| 5,306,268 | 4/1994 | Enloe ...................... 604/385.2 |
| 5,330,458 A | 7/1994 | Buell et al. ............... 604/385.1 |
| 5,358,500 A | 10/1994 | Lavon et al. ............ 604/385.2 |
| 5,368,584 A | 11/1994 | Clear et al. ............... 604/385.2 |
| 5,397,318 A | 3/1995 | Dreier ..................... 604/385.2 |
| 5,415,644 A | 5/1995 | Enloe ...................... 604/385.2 |
| 5,507,736 A | 4/1996 | Clear et al. ............... 604/385.2 |
| 5,509,915 A | 4/1996 | Hanson et al. .............. 604/378 |
| 5,593,401 A * | 1/1997 | Sosalla et al. ........... 604/385.2 |

ABSORBENT ARTICLE HAVING A FIT PANEL

This application claims priority from U.S. Provisional Application No. 60/020,302 filed on Jun. 19, 1996.

BACKGROUND OF THE INVENTION

1. Field of the Invention

The present invention relates to an absorbent article for absorbing body fluids and exudates, such as urine and fecal material. More particularly, the present invention relates to absorbent garments, such as disposable diapers and adult incontinence garments, which include a fit panel for improved fit and performance.

2. Description of the Related Art

Conventional absorbent articles, such as disposable diapers, employ an absorbent chassis assembly which generally includes absorbent materials located between a liquid pervious topsheet and a liquid impermeable backsheet to absorb body exudates. Such conventional absorbent articles have typically included elasticized waistbands and leg cuffs connected to the absorbent chassis assembly to help reduce the leakage of body exudates. Generally, the waistbands and leg cuffs on conventional absorbent articles have been elasticized by employing strands of elastic which have been elongated and attached to the desired region of the article. Some conventional absorbent articles have also included elasticized containment or barrier flaps at the leg or waist sections of the article to further reduce leaks.

Such containment flaps have typically included at least one strand of elastic along the free edge of the flap to maintain the free edge in a spaced apart relationship from the topsheet of the article. Conventional absorbent articles have also included elasticized fastening systems which have been connected to the side edges of the absorbent chassis of the article in one of the waist sections.

However, conventional absorbent articles which incorporate elasticized waistbands or flaps at their waist sections and elasticized fastening systems have not been completely satisfactory. For example, typical waistbands which include elastic strands attached to the waist section of the article in an elongated condition have unduly restricted the movement of the absorbent chassis with respect to the elasticized portions. Such elastic waistbands have undesirably prevented the expansion of the absorbent chassis to receive and contain body exudates. Such waistbands have also generally been narrow, laterally extending strands or strips which have resulted in redmarking and irritation of the wearer's skin. In addition, the narrow waistbands have not always provided a reliable sealing surface with the wearer's body resulting in leakage.

Moreover, the containment or barrier flaps at the waist sections of conventional absorbent articles have typically been constructed for the purpose of creating a pocket for containing body exudates. Thus, such flaps have generally not been designed to provide a comfortable and contouring fit and appearance of the article on the wearer. As a result, some conventional absorbent articles utilizing such flaps have undesirably sagged, gapped or drooped during use due to the movements of the wearer and the downward forces exerted when the article is loaded with body exudates. This sagging and drooping has lead to increased leakage and poor fit of the absorbent article about the waist of the wearer.

Further, although the elasticized fastening systems used on conventional absorbent articles have improved the fit of the article about the wearer, such systems have typically not been tied in or connected to the elasticized waistbands and flaps. Thus, the forces exerted on the fastening system have not been efficiently transferred and distributed laterally across the waist section of the diaper along a wide band. As a result, the fit and containment of conventional absorbent articles have not been completely satisfactory. Accordingly, there remains a need for improved fit and containment at the waist sections of absorbent articles.

SUMMARY OF THE INVENTION

In response to the difficulties and problems discussed above, a new disposable absorbent article which has a fit panel has been discovered.

In one aspect, the present invention relates to an absorbent article having an absorbent chassis which defines a front waist section, a rear waist section, an intermediate section which interconnects the front and rear waist sections, a pair of longitudinally opposed end edges, and a pair of laterally opposed side edges. The absorbent article comprises at least one fit panel attached to said absorbent chassis which defines a waist edge which is superposed adjacent one of the end edges of the absorbent chassis, a pair of laterally opposed outboard edges which are located laterally beyond both of the side edges of the absorbent chassis, and a second edge which is located longitudinally inward from the end edge of the absorbent chassis and which remains at least partially unattached to the waist section of the absorbent chassis. At least a portion of the total panel width and total length of the fit panel remains at least partially unattached to the absorbent chassis between the side edges of the absorbent chassis thereby defining an unattached width. The unattached width is at least about 10 percent of the width of the absorbent chassis. In a particular embodiment, the fit panel remains unattached to the absorbent chassis between said side edges of said absorbent chassis along an unattached width of at least about 10 percent of a width of the absorbent chassis. In another particular embodiment, the fit panel is attached to the absorbent chassis along a lateral attachment zone which is located a distance of from about 0.5 to about 4.0 centimeters longitudinally inward from the end edge of the absorbent chassis.

In another aspect, the present invention relates to an absorbent article having an absorbent chassis which defines a front waist section, a rear waist section, an intermediate section which interconnects the front and rear waist sections, a pair of longitudinally opposed end edges, and a pair of laterally opposed side edges. The absorbent article comprises at least one fit panel which is located in one of the waist sections of the absorbent chassis adjacent the end edge of the absorbent chassis and which extends laterally beyond the side edges of the absorbent chassis. The fit panel comprises a center bridge panel and a pair of laterally opposed side panels which are connected to opposed lateral edges of the bridge panel and which are connected to and extend laterally beyond the side edges of the absorbent chassis. The bridge panel defines a width which is from about 10 to about 90 percent of a width of the absorbent chassis.

In yet another aspect, the present invention relates to an absorbent article having a front waist section, a rear waist section, and an intermediate section which interconnects the front and rear waist sections. The article comprises a backsheet layer, a liquid permeable topsheet layer which is connected in superposed relation to the backsheet layer, an absorbent body and at least one elastomeric fit panel. The absorbent body is located between the topsheet layer and the backsheet layer. A combination of the backsheet layer, the topsheet layer, and the absorbent body define an absorbent chassis which includes an outer perimeter defined by a pair of longitudinally opposed end edges and a pair of laterally opposed side edges. The elastomeric fit panel is connected to the topsheet in one of the waist sections of the absorbent article. The fit panel defines a waist edge which is superposed adjacent the respective end edge of the absorbent chassis, a pair of laterally opposed outboard edges which are located laterally beyond the side edges and the outer perimeter of the absorbent chassis, and a second edge which is located longitudinally inward from the end edge of the absorbent chassis and which remains at least partially unattached to the topsheet of the absorbent article. At least a portion of the total panel width and total length of the fit panel remains at least partially unattached to the absorbent chassis between the side edges of the absorbent chassis thereby defining an unattached width. The unattached width is at least about 10 percent of the width of the absorbent chassis. In a particular embodiment, the elastomeric fit panel extends laterally beyond each of the side edges of the absorbent chassis a distance of at least about 0.5 centimeters.

The various aspects of the present invention can advantageously provide an absorbent article having a more comfortable and contouring fit and appearance about the waist of the wearer.

BRIEF DESCRIPTION OF THE DRAWINGS

The invention will be more fully understood and further advantages will become apparent when reference is made to the following detailed description of the invention and the accompanying drawings, in which.

DETAILED DESCRIPTION OF THE INVENTION

The following detailed description will be made in the context of a disposable diaper article which is adapted to be worn by infants about the lower torso. It is readily apparent, however, that the absorbent article of the present invention would also be suitable for use as other types of absorbent articles, such as feminine care pads, incontinence garments, training pants, and the like. In addition, the invention will be described in the context of its various configurations. It should be appreciated that alternative arrangements of the invention can comprise any combination of such configurations.

Figure 1:
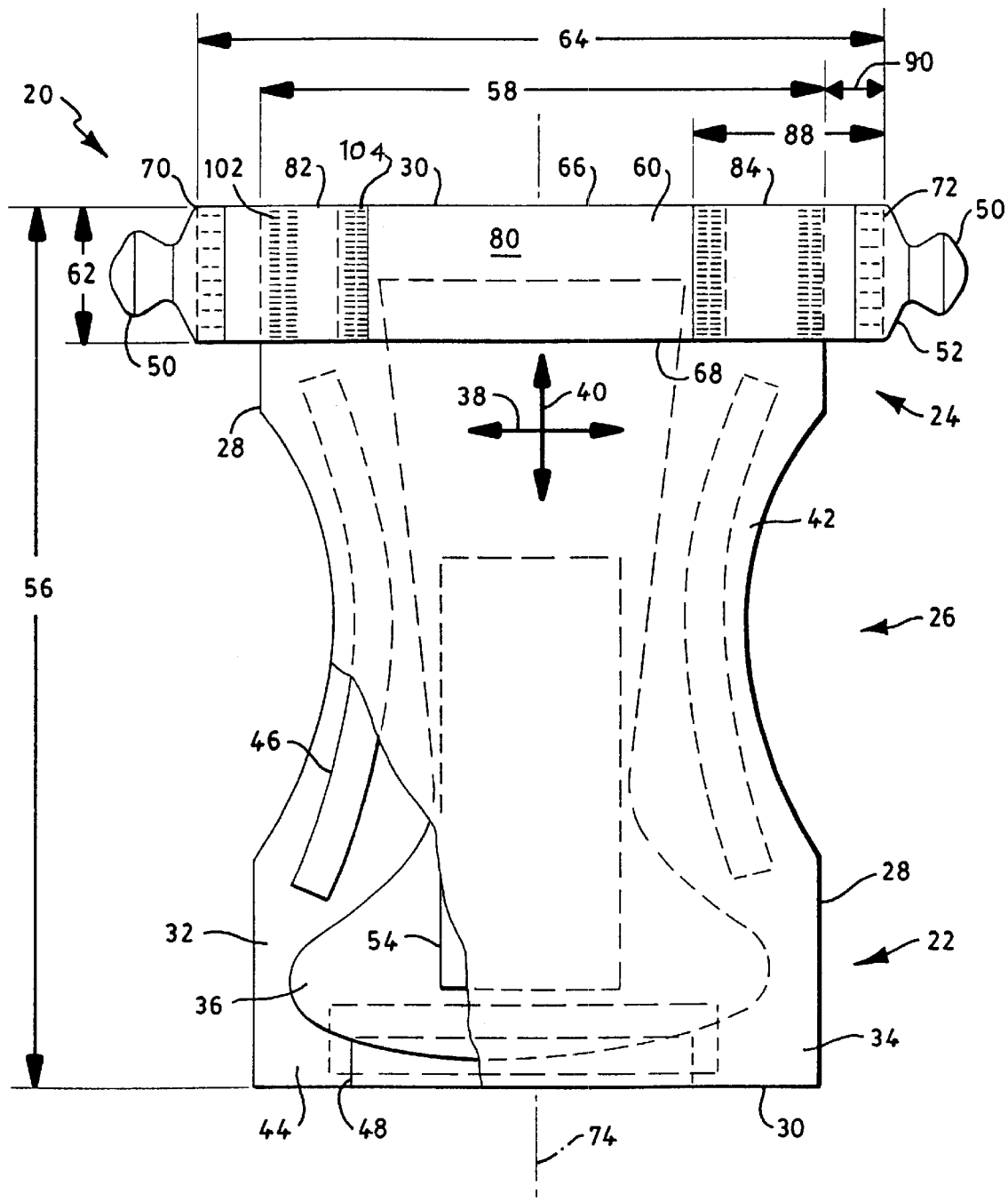
FIG. 1 representatively shows a partially cut away, top plan view of an absorbent article according to one embodiment of the invention.
Figure 2:
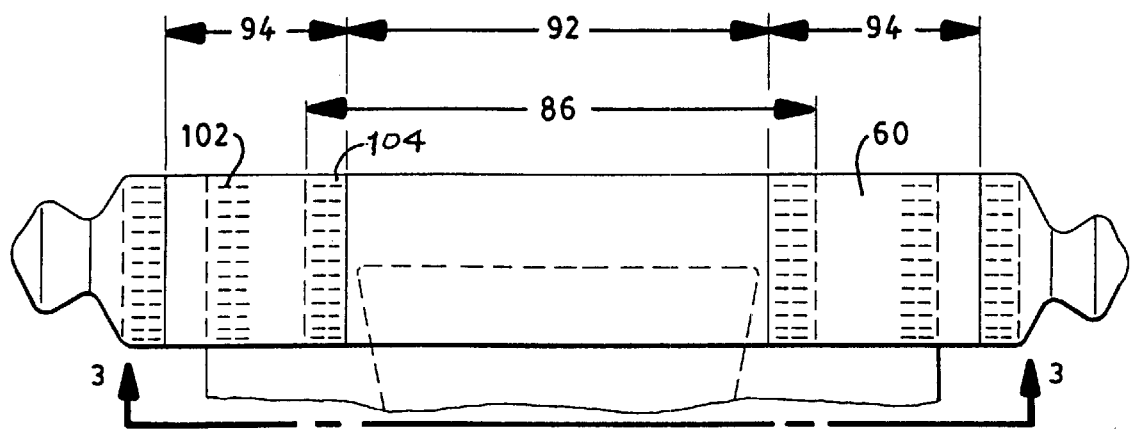
FIG. 2 representatively shows a top plan view of a portion of the absorbent article of FIG. 1.
Figure 3:
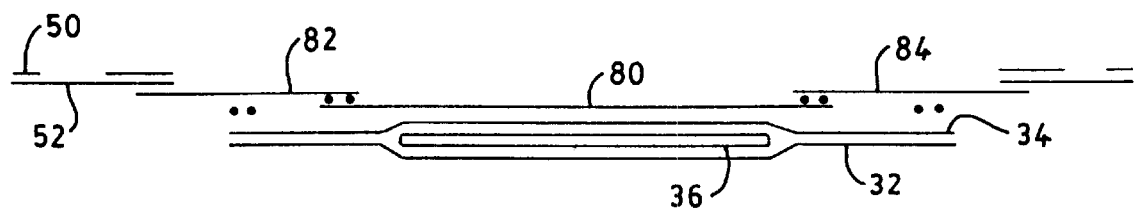
FIG. 3 representatively shows a sectional view of the absorbent article of FIG. 2 taken along line 3—3.

With reference to FIGS. 1–3, an integral absorbent garment article, such as the disposable diaper 20, generally defines an absorbent chassis which has a front waist section 22, a rear waist section 24, an intermediate section 26 which interconnects the front and rear waist sections, a pair of laterally opposed side edges 28, and a pair of longitudinally opposed end edges 30. The front and rear waist sections include the general portions of the article which are constructed to extend substantially over the wearer's front and rear abdominal regions, respectively, during use. The intermediate section of the article includes the general portion of the article which is constructed to extend through the wearer's crotch region between the legs. The opposed side edges 28 define leg openings for the article and generally are curvilinear or contoured to more closely fit the legs of the wearer. The opposed end edges 30 define a waist opening for the article and typically are straight but may also be curvilinear.

FIG. 1 is a representative plan view of the diaper 20 of the present invention in a flat, uncontracted state. Portions of the structure are partially cut away to more clearly show the interior construction of the diaper 20, and the surface of the diaper which contacts the wearer is facing the viewer. The diaper 20 generally defines an absorbent chassis which includes a substantially liquid impermeable backsheet 32, a porous, liquid permeable topsheet 34 positioned in facing relation with the backsheet 32, and an absorbent body 36, such as an absorbent pad, which is located between the backsheet and the topsheet. The diaper 20 also defines a lateral direction 38 and a longitudinal direction 40. Marginal portions of the diaper 20, such as marginal sections of the backsheet 32, may extend past the terminal edges of the absorbent body 36. In the illustrated embodiment, for example, the backsheet 32 extends outwardly beyond the terminal marginal edges of the absorbent body 36 to form side margins 42 and end margins 44 of the diaper 20. The topsheet 34 is generally coextensive with the backsheet 32 but may optionally cover an area which is larger or smaller than the area of the backsheet 32, as desired. The backsheet 32, topsheet 34, and absorbent body 36 generally define the absorbent chassis which has a length 56 and width 58 corresponding to the distance between outermost edges of the backsheet 32 and/or topsheet 34 in the longitudinal 40 and lateral direction 38, respectively. The outermost edges of the backsheet 32 and/or topsheet 34 further define an outer perimeter of the absorbent chassis.

To provide improved fit and to help reduce leakage of body exudates from the diaper 20, the side margins 42 and at least one of the end margins 44 of the diaper may be elasticized with suitable elastic members, such as leg elastic members 46 and waist elastic member 48. For example, the leg elastic members 46 may include single or multiple strands of elastic or elastomeric composites which are constructed to operably gather and shirr the side margins 42 of the diaper 20 to provide elasticized leg bands which can closely fit around the legs of the wearer to reduce leakage and provide improved comfort and appearance. Similarly, the waist elastic member 48 can be employed to elasticize at least one of the end margins 44 of the diaper 20 to provide an elasticized waistband. The waist elastics are configured to operably gather and shirr the waistband sections to provide a resilient, comfortably close fit around the waist of the wearer.

The elastic members 46 and 48 are secured to the diaper 20 in an elastically contractible condition so that in a normal under strain configuration, the elastic members effectively contract against the diaper 20. For example, the elastic members 46 and 48 may be elongated and secured to the diaper 20 while the diaper is in an uncontracted condition. In FIG. 1, the elastic members 46 and 48 are illustrated in their uncontracted, stretched condition for the purpose of clarity. Alternatively, the diaper 20 may include a pair of separate, elasticized and gathered leg gussets (not shown) which are attached to the diaper along the side margins 42 in at least the intermediate section 26 of the diaper 20 to provide elasticized leg cuffs. Such leg gussets may be configured to extend beyond and bridge across the respective concave portion of the side margins 42.

The diaper 20, as representatively illustrated in FIGS. 1–3, may further include a pair of fasteners 50 which are employed to secure the diaper 20 about the waist of a wearer. Suitable fasteners 50 include hook-and-loop type fasteners, adhesive tape fasteners, buttons, pins, snaps, mushroom-and-loop fasteners, and the like. A cooperating side panel member 52 can be associated with each fastener and may be constructed to be nonelasticized, or to be elastically stretchable at least along the lateral direction 38 of the diaper 20.

The diaper 20 may also include a pair of elasticized, longitudinally extending containment flaps (not shown) which are configured to maintain an upright, perpendicular arrangement in at least the intermediate section 26 of the diaper 20 to serve as an additional barrier to the lateral flow of body exudates. The diaper 20 may further include a surge management layer 54 positioned between the topsheet 34 and the absorbent body 36 which is configured to efficiently hold and distribute liquid exudates to the absorbent body 36. The surge management layer 54 can prevent the liquid exudates from pooling and collecting on the portion of the diaper positioned against the wearer's skin, thereby reducing the level of skin hydration. Suitable constructions and arrangements of containment flaps and surge management layers are well known to those skilled in the art. Other suitable diaper components may also be incorporated on absorbent articles of the present invention.

The diaper 20 may be of various suitable shapes. For example, the diaper may have an overall rectangular shape, T-shape or an approximately hour-glass shape. In the shown embodiment, the diaper 20 has a generally I-shape. Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996, to Hanson et al., the disclosures of which are herein incorporated by reference to the extent they are consistent herewith. The various aspects and configurations of the invention can provide distinctive combinations of softness, body conformity, reduced red-marking of the wearer's skin, reduced skin hydration, and improved containment of body exudates.

The various components of the diaper 20 are integrally assembled together employing various types of suitable attachment means, such as adhesive, ultrasonic bonds, thermal bonds or combinations thereof. In the shown embodiment, for example, the topsheet 34 and backsheet 32 are assembled to each other and to the absorbent body 36 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, other diaper components, such as the elastic members 46 and 48 and the fasteners 50, may be assembled into the diaper article by employing the above-identified attachment mechanisms.

The backsheet 32 of the diaper 20, as representatively illustrated in FIGS. 1–3, may suitably be composed of a material which is either liquid permeable or liquid impermeable. It is generally preferred that the backsheet 32 be formed from a material which is substantially impermeable to liquids. For example, a typical backsheet can be manufactured from a thin plastic film or other flexible liquid-impermeable material. For example, the backsheet 32 may be formed from a polyethylene film having a thickness of from about 0.012 millimeter (0.5 mil) to about 0.051 millimeter (2.0 mils). If it is desired to present the backsheet with a more clothlike feeling, the backsheet 32 may comprise a polyolefin film having a nonwoven web laminated to the outer surface thereof, such as a spunbond web of polyolefin fibers. For example, a stretch-thinned polypropylene film having a thickness of about 0.015 millimeter (0.6 mil) may have thermally laminated thereto a spunbond web of polypropylene fibers, which fibers have a thickness of about 1.5 to 2.5 denier per filament, which nonwoven web has a basis weight of about 17 grams per square meter (0.5 ounce per square yard). Methods of forming such clothlike backsheets are known to those skilled in the art.

Further, the backsheet 32 may be formed of a woven or nonwoven fibrous web layer which has been totally or partially constructed or treated to impart a desired level of liquid impermeability to selected regions that are adjacent or proximate the absorbent body 36. Still further, the backsheet 32 may optionally be composed of a micro-porous "breathable" material which permits vapors to escape from the absorbent body 36 while still preventing liquid exudates from passing through the backsheet 32. The backsheet 32 typically provides the outer cover of the diaper 20. The backsheet 32 can also be embossed or otherwise provided with a matte finish to provide a more aesthetically pleasing appearance.

The topsheet 34, as representatively illustrated in FIGS. 1–3, suitably presents a bodyfacing surface which is compliant, soft feeling, and nonirritating to the wearer's skin. Further, the topsheet 34 may be less hydrophilic than the absorbent body 36, to present a relatively dry surface to the wearer, and may be sufficiently porous to be liquid permeable, permitting liquid to readily penetrate through its thickness. A suitable topsheet 34 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet 34 is suitably employed to help isolate the wearer's skin from liquids held in the absorbent body 36.

Various woven and nonwoven fabrics can be used for the topsheet 34. For example, the topsheet may be composed of a meltblown or spunbonded web of polyolefin fibers. The topsheet may also be a bonded-carded web composed of natural and/or synthetic fibers. The topsheet may be composed of a substantially hydrophobic material, and the hydrophobic material may, optionally, be treated with a surfactant or otherwise processed to impart a desired level of wettability and hydrophilicity. In a particular embodiment of the present invention, the topsheet 34 comprises a nonwoven, spunbond, polypropylene fabric composed of about 2.8–3.2 denier fibers formed into a web having a basis weight of about 20 grams per square meter and a density of about 0.13 gram per cubic centimeter. The fabric may be surface treated with about 0.28 weight percent of a surfactant commercially available from the Rohm and Haas Co. under the trade designation TRITON X-102. The surfactant may be applied by any conventional means, such as spraying, printing, brush coating or the like. The surfactant may be applied to the entire topsheet 34 or may be selectively applied to particular sections of the topsheet 34, such as the medial section along the longitudinal centerline of the diaper, to provide greater wettability of such sections.

The absorbent body 36 of the diaper 20, as representatively illustrated in FIGS. 1–3, may suitably comprise a matrix of hydrophilic fibers, such as a web of cellulosic fluff, mixed with particles of a high-absorbency material commonly known as superabsorbent material. In a particular embodiment, the absorbent body 36 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. The fluff and superabsorbent particles may also be selectively placed into desired zones of the absorbent body 36 to better contain and absorb body exudates. The concentration of the superabsorbent particles may also vary through the thickness of the absorbent body 36. Alternatively, the absorbent body 36 may comprise a laminate of fibrous webs and superabsorbent material or other suitable means of maintaining a superabsorbent material in a localized area.

The absorbent body 36 may have any of a number of shapes. For example, the absorbent core may be rectangular, I-shaped, or T-shaped. It is generally preferred that the absorbent body 36 be narrower in the crotch area than in the front or rear portions of the diaper 20. The size and the absorbent capacity of the absorbent body 36 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va. and DOW DRYTECH 2035LD polymer available from Dow Chemical Co. located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent body 36.

Optionally, a substantially hydrophilic tissue wrapsheet (not illustrated) may be employed to help maintain the integrity of the airlaid fibrous structure of the absorbent body 36. The tissue wrapsheet is typically placed about the absorbent body over at least the two major facing surfaces thereof and composed of an absorbent cellulosic material, such as creped wadding or a high wet-strength tissue. In one aspect of the invention, the tissue wrapsheet can be configured to provide a wicking layer which helps to rapidly distribute liquid over the mass of absorbent fibers comprising the absorbent body. In another aspect of the invention, the wrapsheet material on one side of the absorbent fibrous mass may be bonded to the wrapsheet located on the opposite side of the fibrous mass.

The diaper 20 of the different aspects of the present invention further includes at least one fit panel located in at least one of the waist sections 22 and 24 which provides a more comfortable, contouring fit about the wearer. The absorbent article may include a fit panel disposed in both waist sections 22 and 24 and desirably the absorbent article includes a fit panel in at least the rear waist section 24. Desirably, the fit panel is elastomeric. For example, as representatively illustrated in FIGS. 1–7, the diaper 20 includes an elastomeric fit panel 60 which is configured to elongate in the lateral direction 38 to provide an improved fit and appearance of the absorbent article about the wearer by initially providing a conforming fit about the wearer and maintaining such fit throughout the use of such article. The fit panel is also configured such that the absorbent chassis has the ability to expand, contract and receive body exudates without adversely affecting the positioning of the fit panel and the article about the waist of the wearer. Thus, with such a fit panel, movements of the wearer may move the absorbent chassis but do not adversely affect the overall positioning of the article on the wearer. Such improved fit results in reduced leakage from the waist sections of the absorbent article and a more aesthetically pleasing appearance.

The fit panel 60 of the different embodiments of the present invention may be provided in a variety of ways. For example, the fit panel 60 may be a single piece of material or a combination of individual pieces or panels of material attached to the absorbent article using conventional attachment mechanisms such as those described above. The fit panel 60 may also comprise elastic composite materials or non-stretchable materials which have been rendered elastically contractible by means known to those skilled in the art. It also is generally preferred that the fit panel 60 be formed from a material which is substantially impermeable to liquids and which provides a more clothlike feeling. Such a material is capable of maintaining a close conforming fit while not irritating the skin of the wearer.

The fit panel 60 is desirably secured to the absorbent chassis of the diaper 20 such that the width of the fit panel 60 between the points at which it is attached to the absorbent chassis is less than a fully extended width of the absorbent chassis. For example, if the fit panel 60 comprises an elastomeric material, the fit panel 60 may be secured to the absorbent chassis of the diaper in an elastically contractible condition such that in an unstrained configuration, the fit panel 60 effectively contracts the diaper 20. As a result, the fit panel 60 is able to snugly fit the wearer's body independent of the absorbent chassis and any forces exerted on the chassis due to movements of the wearer and loading. To provide such a configuration, the fit panel 60 may be elongated and attached to the absorbent chassis of the diaper 20 while the chassis of the diaper is in an uncontracted condition. Alternatively, the fit panel 60 may be secured to the absorbent chassis of the diaper when the absorbent chassis is in a tucked or pleated condition. Desirably, the fit panel 60 is secured to the absorbent chassis of the diaper 20 such that, in an unstrained configuration, the absorbent chassis of the diaper is gathered from about 3 to about 50 percent, more desirably from about 5 to about 30 percent, and most desirably from about 7 to about 20 percent. As a result, if the fit panel is elastomeric, the portion of the fit panel 60 between the side edges 28 of the absorbent chassis of the diaper 20 where it is attached to the absorbent chassis may be capable of elongating in the lateral direction from a relaxed condition until the absorbent chassis is extended to its full width to provide the improved fit and containment.

As illustrated, the fit panel 60 also extends beyond the side edges 28 of the absorbent chassis of the diaper 20 and is generally coterminous with the end edge 30 of the chassis of the diaper 20 in the respective waist section 22 or 24. Alternatively, as representatively illustrated in FIGS. 5A and 6A, the fit panel 60 may extend longitudinally beyond the end edge 30 of the chassis of the diaper 20 or the end edge 30 of the chassis of the diaper 20 may extend longitudinally beyond the fit panel 60. In a particular embodiment, the waist edge 66 of the fit panel 60 extends longitudinally beyond the end edge of the absorbent chassis to provide improved seals against the body of the wearer. In the illustrated embodiments, the fit panel 60 defines a total length 62, a total panel width 64, a waist edge 66, and a pair of laterally opposed outboard edges 70 and 72 which extend laterally beyond the side edges 28 of the absorbent chassis. The fit panel 60 also defines a second edge 68 which extends longitudinally inward towards the intermediate section 26 of the diaper 20. The second edge 68 of the fit panel 60 is configured to remain at least partially unattached to the topsheet 34 or absorbent chassis of the diaper 20 when in use to allow the absorbent chassis to move and expand to receive and contain body exudates. The unattached second edge 68 may also form a pocket between the fit panel and the absorbent chassis which is configured to further contain body exudates. As representatively illustrated in FIG. 7, the second edge 68 of the fit panel 60 may be curvilinear, such as concave, to better fit the wearer. The waist edge 66 of the fit panel 60 may also be curvilinear to better fit the wearer. Desirably, if the second edge 68 is curvilinear, the waist edge 66 is also curvilinear such that consecutive fit panels 60 for multiple articles nest within each other and can be provided from a continuous sheet of material. In such a configuration, the second edge 68 of the first fit panel corresponds to the waist edge 66 of the next fit panel to improve manufacturing and reduce waste.

The fit panel 60 generally defines a total length 62 which is sufficient to effectively distribute the fastening forces across a wide cross sectional area to provide improved fit without excessive irritation of the skin of the wearer. Desirably, the fit panel 60 defines a total length 62 which is at least about 5 percent and more desirably from about 10 to about 30 percent of the length 56 of the article. Lengths less than the above specified ranges do not provide the improved fit and appearance of the article on the wearer and may result in excessive red marking. Whereas, lengths greater than the above specified ranges may extend too far into the intermediate section 26 of the article such that the fit panel 60 may interfere with the deposition of body exudates into the diaper article.

The fit panel 60 extends laterally across the diaper 20 extending beyond the side edges 28 of the absorbent chassis. In particular, the fit panel defines a total panel width 64 which is greater than the width 58 of the absorbent chassis to which the fit panel 60 is attached to provide the improved fit and performance. As used herein, the width 58 of the absorbent chassis refers to the distance between the outermost portions of the backsheet and/or topsheet layer in the lateral direction 38. In a particular embodiment, the fit panel 60 defines a total panel width 64 which is at least about 105 percent, desirably at least about 115 percent and more desirably at least about 125 percent of the width 58 of the chassis of the diaper 20. For example, the fit panel 60 may define a total panel width 64 of from about 105 to about 150 percent of the width 58 of the absorbent chassis of the diaper 20. Widths less than the above specified ranges do not provide the improved fit and appearance of the diaper 20 on the wearer.

It is further desired that the fit panel 60 extend laterally beyond the side edges 28 of the absorbent chassis of the diaper 20 a distance 90 which is at least about 2 percent and more desirably from about 5 to about 20 percent of the width 58 of the absorbent chassis in the respective waist section. For example, the distance 90 to which the fit panel 60 extends beyond the side edges 28 of the absorbent chassis on a diaper article intended to be worn by a medium sized infant weighing from about 16 to about 28 pounds is at least about 0.5 centimeters and desirably from about 1 to about 5 centimeters.

The portions of the fit panel 60 which extend laterally beyond the side edges 28 of the absorbent chassis of the diaper 20 desirably provide elasticized portions of the fit panel 60 which are not restrained in any manner by the absorbent chassis of the absorbent article. Thus, the portions of the fit panel extending beyond the side edges can be easily stretched around the hips of the wearer to provide a conforming, reliable fit about the wearer. If the distance 90 to which the fit panel 60 extends beyond the side edges 28 of the absorbent chassis is too short, the fit panel 60 may be undesirably restrained by the width 58 of the absorbent chassis at the respective waist section resulting in a less than optimum fit about the wearer.

As set forth above, the fit panel 60 may be a single unitary piece or layer of material or a combination or laminate of materials. In the embodiments representatively illustrated in FIGS. 1–6A, the fit panel 60 generally defines a bridge panel 80 which is flanked by and connected to a pair of laterally opposed side panels 82 and 84 along respective attachment zones 104. The side panels 82 and 84 are connected to and extend outwardly in a lateral direction 38 from the bridge panel 80 beyond the side edges 28 of the absorbent chassis of the diaper 20. In use, the bridge panel 80 is generally configured to be located on the front or back abdominal regions of the wearer while the side panels 82 and 84 are generally configured to be located on the side hip regions of the wearer. In such a configuration, the particular location, size and elastic nature of each panel of the fit panel 60 is important to the performance of the fit panel 60 in use.

On the majority of typical wearers of such absorbent articles and, in particular, on infants, the small or central portion of the wearer's back is generally concave (bowed inwards) or flat in shape and the front abdominal region of the wearer is generally convex or curved outwards. As a result, it has been difficult to maintain a tight seal between the absorbent article and the wearer in these areas. Depending upon whether the fit panel 60 of the present invention is located in the front or rear waist sections 22 and 24 of the diaper 20, the bridge panel 80 of the fit panel 60 corresponds to the area of the fit panel 60 which is intended to be in contact with either the small of the wearer's back or the outwardly curved front abdominal region when in use. The bridge panel 80 is configured to provide a conforming fit of the fit panel 60 to these locations on the wearer.

As representatively illustrated in FIGS. 1–6A, the bridge panel 80 of the fit panel 60 is typically centered about the longitudinal centerline 74 of the diaper 20 and defines a width 86 which generally corresponds to the width of the small of the wearer's back or front abdominal region of the wearer. For example, the width 86 of the bridge panel 80 of the fit panel 60 may be from about 10 to about 90 percent and desirably from about 30 to about 70 percent of the width 58 of the absorbent chassis of the article. In a particular embodiment, the width 86 of the bridge panel 80 is at least about 10 percent, desirably at least about 25 percent, and more desirably at least about 40 percent of the width 58 of the absorbent chassis of the article. For example, the width 86 of the bridge panel 80 on a diaper article which is intended to be worn by a medium-sized infant weighing from about 16 to about 28 pounds may be from about 10 to about 15 centimeters. Width dimensions less than the above specified ranges are not sufficient to extend along the entire width of the small of the wearer's back or the wearer's front abdominal region.

The side panels 82 and 84 of the fit panel 60 are generally the areas of the fit panel 60 which are intended to be in contact with the convex surface of the outer hip regions of the wearer when in use. As representatively illustrated in FIGS. 1–6A, the side panels 82 and 84 of the fit panel 60 are attached to and laterally flank the bridge panel 80 of the fit panel 60. The illustrated side panels 82 and 84 are also attached to and extend laterally beyond the side edges 28 of the absorbent chassis of the article. Each of the side panels 82 and 84 defines a width 88 which generally corresponds to the width of the portions of the diaper article which are intended to be positioned on the hip regions of the wearer in use. For example, the width 88 of each side panel 82 and 84 may be from about 10 to about 70 percent and desirably from about 35 to about 50 percent of the width 58 of the absorbent chassis of the article.

In the embodiments illustrated in FIGS. 1–6A, the side panels 82 and 84 of the fit panel also extend laterally inward from the side edges 28 of the absorbent chassis to the bridge panel 80. The distance the side panels extend inwardly will vary depending upon the desired width 86 of the bridge panel 80. In a particular embodiment wherein the absorbent article includes a pair of longitudinally extending containment flaps located between the side edges of the article, it is further desired that the side panels 82 and 84 of the fit panel 60 extend laterally inwardly from the side edges 28 at least to the respective containment flap for improved performance.

Each of the panels 80, 82 and 84 of the fit panel 60 representatively illustrated in FIGS. 1–6A are desirably elastomeric or extensible in the lateral direction 38 to stretchably fit and conform to the waist region of the wearer to provide the improved fit and performance. The elastic nature or properties of each panel are designed such that the fit panel is capable of expanding and contracting with the movements of the wearer to enhance the fit of the article on the wearer. For example, the side panels 82 and 84 of the fit panel 60 may be configured to be more elastic or stretchable than the bridge panel 80. Alternatively, the bridge panel 80 of the fit panel 60 may be more stretchable than the side panels 82 and 84. Such arrangements will depend upon several factors including the general size and shape of the intended wearer, the intended loading of the article on the wearer, and the size, shape and dimensions of the different panel sections of the fit panel. As representatively illustrated in FIGS. 1–6A, the different elastic properties of the bridge panel 80 and the side panels 82 and 84 may define a central zone of elasticity 92 and a pair of side zones of elasticity 94 which are configured to provide the improved fit and performance.

In a particular embodiment, the side panels 82 and 84 of the fit panel 60 are configured to be more elastic or stretchable in the lateral direction 38 than the bridge panel 80 such that the side panels 82 and 84 can easily stretch about the hips of the wearer to provide a more optimum fit and seal. For example, the side panels 82 and 84 may be configured to elongate in the lateral direction a greater percentage than said bridge panel 80 when a lateral force is exerted on the fit panel 60. In such a configuration, the side panels 82 and 84 and side zones of elasticity 94 of the fit panel 60 are configured to elongate in the lateral direction 38 when the diaper article is fit about the hips of a wearer and fastened thereto. Specifically, the side panels 82 and 84 and side zones of elasticity are configured to exert a force about the convex surface of the outer hip regions of the wearer to provide a close-to-the body fit and reliably maintain the diaper about the waist of the wearer. The elastic properties of the side panels 82 and 84 of the fit panel 60 are also configured to distribute most of the forces exerted by the fasteners and any movements of the wearer such that such forces do not adversely affect the positioning and movement of the absorbent chassis of the diaper 20. Thus, the absorbent chassis is allowed to freely expand and move relative to the fit panel 60 to reliably contain body exudates while the fit panel 60 maintains the diaper 20 about the waist of the wearer. To provide such elastic properties, each side panel 82 and 84 is generally capable of being elongated in the lateral direction 38 from about 10 to about 350 percent, desirably from about 25 to about 300 percent, and more desirably from about 50 to about 250 percent from a relaxed condition.

It has been also discovered that diapers having such a fit panel which is located in the rear waist section 24 of the diaper 20 are easier to fasten about a wearer. To fasten conventional absorbent articles about a wearer, the wearer typically is placed back down on the rear waist portion of the absorbent article and the front waist portion is brought upward between the legs of the wearer and positioned on the front abdominal region of the wearer. The side edges of the absorbent article at the front and rear waist sections are then fastened together to secure the article on the wearer. It has been discovered that having the location of the more stretchable portions of the fit panel 60 at the side edges improves the positioning and fastening of the article about the wearer which provides an optimum fit and reduces leaks. Such improvements are realized because the portions of the fit panel 60 which are configured to stretch the most, the side panels 82 and 84 and respective side zones of elasticity 94 of the present invention, are not subjected to the weight of the wearer in the fastening process. Whereas, in conventional absorbent articles which have included rear waist flaps having elastic portions across the center of the flap and article, the weight of the wearer on the elastic portions has adversely affected the ability to properly position and fasten the article about the wearer on the initial fastening.

The fit panel 60 as representatively illustrated in FIGS. 1–6A can be provided in any suitable manner which provides the desired fit properties and performance. Desirably, the fit panel 60 includes an elastomeric material. For example, the bridge panel 80 and side panels 82 and 84 may be provided by three individual pieces of elastomeric material which are joined together along their side edges to provide the fit panel 60. The materials may include a stretch-bonded-laminate (SBL) material, a neck-bonded-laminate (NBL) material, an elastomeric film, an elastomeric foam material, or the like. For example, suitable meltblown elastomeric fibrous webs are described in U.S. Pat. No. 4,663,220, issued May 5, 1987 to T. Wisneski et al., the disclosure of which is hereby incorporated by reference. Examples of composite fabrics comprising at least one layer of a nonwoven material secured to a fibrous elastic layer are described in European Patent Application NO. EP 0 110 010 published on Apr. 8, 1987 with the inventors listed as J. Taylor et al., the disclosure of which is hereby incorporated by reference. Examples of NBL materials are described in U.S. Pat. No. 5,226,992 issued Jul. 13, 1993 to Mormon, the disclosure of which is hereby incorporated by reference.

Figure 7:
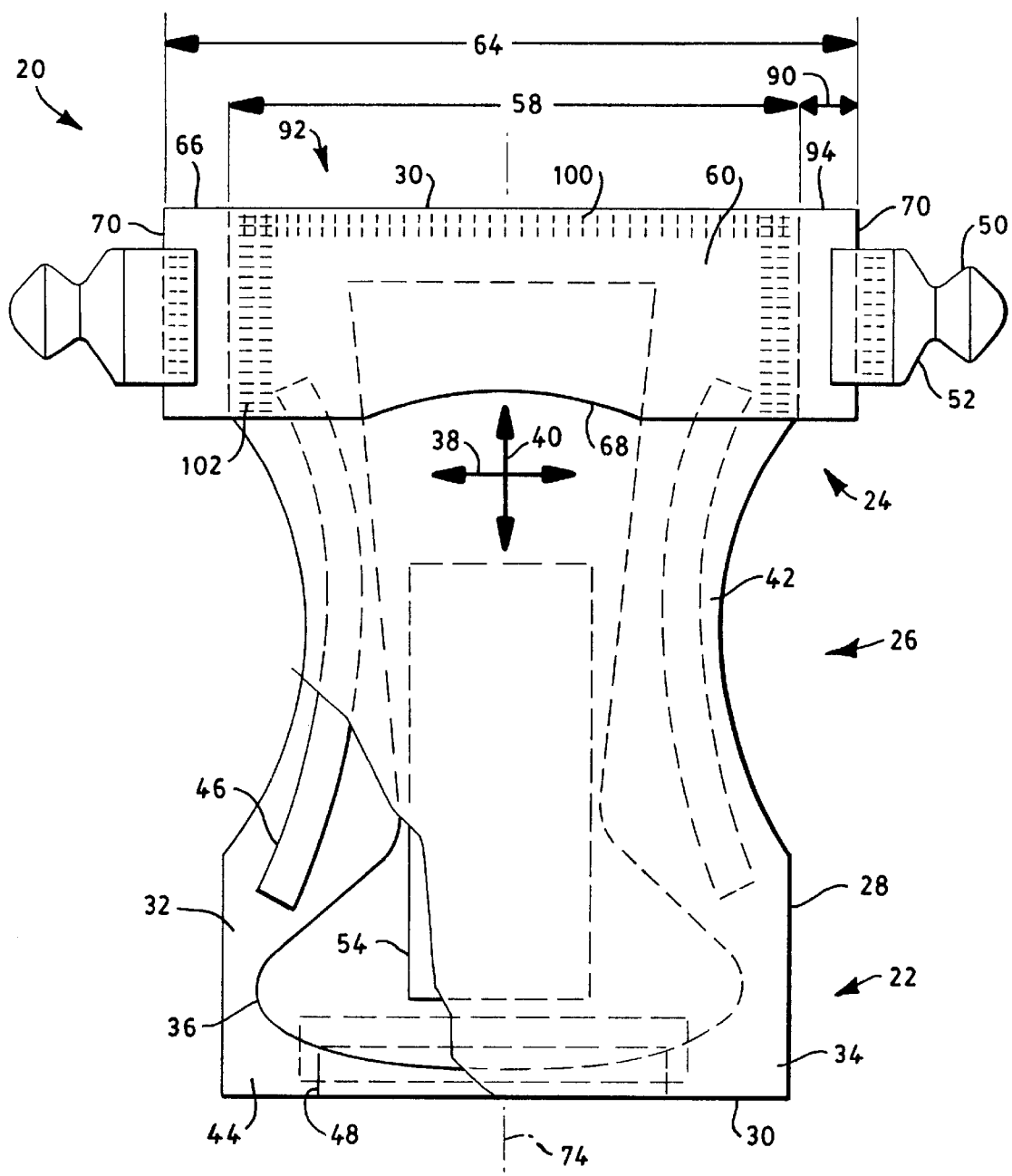
FIG. 7 representatively shows a partially cut away, top plan view of an absorbent article according to yet another embodiment of the invention.

Alternatively, as representatively illustrated in FIG. 7, the fit panel 60 may include a single piece of elastomeric material. The elastomeric material may include a stretch-bonded-laminate (SBL) material, a neck-bonded-laminate (NBL) material, an elastomeric film, an elastomeric foam material, or the like as well as combinations thereof as described above. Such a single piece of material may be modified in the area of the central zone of elasticity 92 or side zones of elasticity 94 to provide the desired elastic properties. The elastic properties of the respective areas of the elastomeric material which provide the central or side zones of elasticity may be modified in any suitable manner. For example, in a particular embodiment, the elastic properties of portions of the fit panel 60 may be modified by bonding the material at specific locations to render such bonded areas less elastic than the unbonded areas. The effect the bonding has on the elastic properties of the material can depend upon several factors including the area of the bonding or the bond point density. Desirably, the bond point density in the bonding zones is from about 3 to about 50 percent and desirably from about 5 to about 30 percent of the area of the bonding zone to provide a reduction in the elastic properties of the material while not completely destroying the elastic properties of the material.

In a particular embodiment wherein the fit panel 60 includes an elastomeric material, it is desirable that the fit panel 60 be capable of providing an elongation in the lateral direction of at least about 5 percent, more desirably at least about 15 percent, and even more desirably at least about 30 percent when subjected to a tensile force load of about 80 grams in the lateral direction 38 per lineal centimeter of the sample measured in the longitudinal direction 40. Moreover, it is also desirable that the fit panel 60 be capable of providing a tension range of from about 20 to about 400 grams, more desirably from about 40 to about 275 grams, and even more desirably from about 60 to about 200 grams per lineal centimeter of the sample measured in the longitudinal direction 40 when subjected to an elongation of 30 percent in the lateral direction 38.

In another alternative configuration, the fit panel 60 may be provided by a substantially non-elastomeric material, such as polymer films, woven fabrics, non-woven fabrics, or the like such as described above as being suitable for the backsheet 32 or topsheet 34. For example, the fit panel may include a polyethylene film having a nonwoven web laminated to the outer surface thereof. The fit panel 60 may also be formed of a woven or nonwoven fibrous web layer which has been totally or partially constructed or treated to impart a desired level of liquid impermeability, or wettability and hydrophilicity. Still further, the fit panel 60 may optionally be composed of a micro-porous "breathable" material which permits vapors to escape from between the fit panel 60 and the topsheet 34 of the diaper 20.

Such a fit panel may also be modified to render portions elastically contractible to provide the desired elastic properties to the fit panel 60. For example, the fit panel 60 and, in particular, the bridge panel 80 and side panels 82 and 84 or respective zones of elasticity 92 and 94 of the fit panel 60 may be made elastic or stretchable by means well known to those skilled in the art. For example, the different portions of the fit panel 60 may include a plurality of elastic strands which are elongated and adhesively attached in the lateral direction 38 to the respective portions of the fit panel 60. Suitable elastic strands are known to those skilled in the art. For example, a suitable elastic strand may be composed of a 470 decitex LYCRA elastomer or a 620 decitex LYCRA elastomer commercially available from E. I. DuPont de Nemours Co., a business having offices located in Wilmington, Del., or other elastomers with suitable characteristics. Alternatively, a piece of elastic material may be adhesively attached to the respective portions of the fit panel 60 in an elongated condition to provide the desired stretchability. The elastic material may include a stretch-bonded-laminate (SBL) material, a neck-bonded-laminate (NBL) material, an elastomeric film, an elastomeric foam material, or the like as described above.

The fit panel 60 of the different embodiments of the present invention may be attached to the absorbent chassis of the diaper 20 in any suitable manner which provides the desired properties. For example, the fit panel 60 may be attached to the absorbent chassis using adhesive, ultrasonic, thermal bonding techniques and the like or combinations thereof. The fit panel 60 may be attached to the absorbent chassis of the diaper 20 along a lateral attachment zone 100 as representatively illustrated in FIGS. 4–7, and a pair of opposed longitudinal attachment zones 102 as representatively illustrated in FIGS. 1, 2 and 4–7. The lateral attachment zone 100 is generally located along or near the end edge 30 of the absorbent chassis of the diaper 20 while the longitudinal attachment zones 102 are located along the side edges 28 of the absorbent chassis in the respective waist section of the diaper 20. The lateral and longitudinal attachment zones 100 and 102, respectively, generally extend in the lateral and longitudinal directions 38 and 40, respectively, but may otherwise extend at angles from the lateral and longitudinal directions depending upon the configuration of the fit panel and the desired distribution of forces across the fit panel. Such angled attachment zones can result in improved fit.

Figure 4:
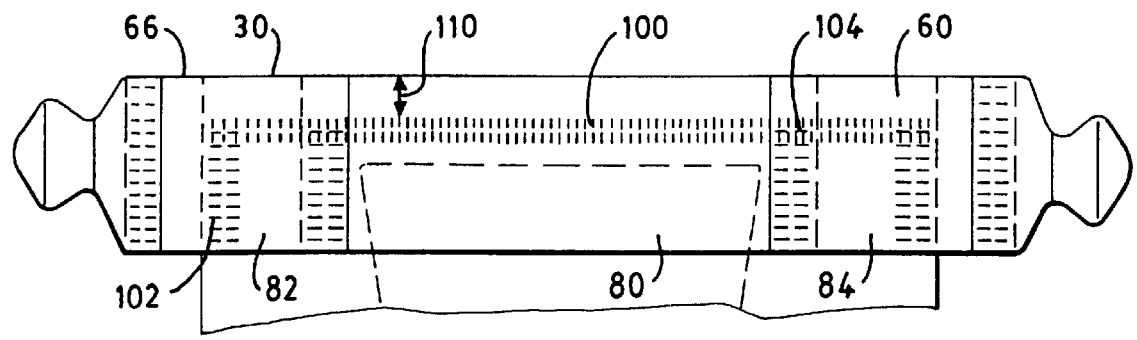
FIG. 4 representatively shows a top plan view of a portion of an absorbent article according to another embodiment of the invention.

In one particularly preferred embodiment as illustrated in FIG. 4, the fit panel 60 may be attached to the topsheet 34 of the diaper 20 along a lateral attachment zone 100 which is located a distance 110 longitudinally inward from the end edge 30 of the absorbent chassis diaper 20 and the respective waist edge 66 of the fit panel 60. It has been discovered that locating the lateral attachment zone 100 inward a distance 110 of at least about 0.5 centimeters, desirably from about 0.5 to about 4.0 centimeters, and more desirably from about 1.0 to about 4.0 centimeters allows the unattached portions located outward of the attachment zone 100 to stretch to provide a more conforming fit. In addition, It has been discovered that such a location of the lateral attachment zone 100 also provides improved distribution of the forces exerted by the fasteners 50 across the width and length of the fit panel because the attachment zone 100 is located on or adjacent to a laterally extending path of force between the fasteners 50. The improved distribution of forces reduces the amount of buckling and wrinkling of the fit panel resulting in improved performance and aesthetic appearance.

Figure 5:
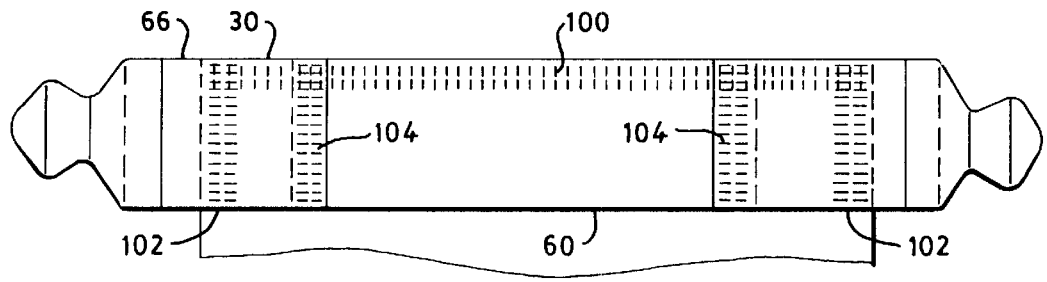
FIG. 5 representatively shows a top plan view of a portion of an absorbent article according to another embodiment of the invention.
Figure 5A:
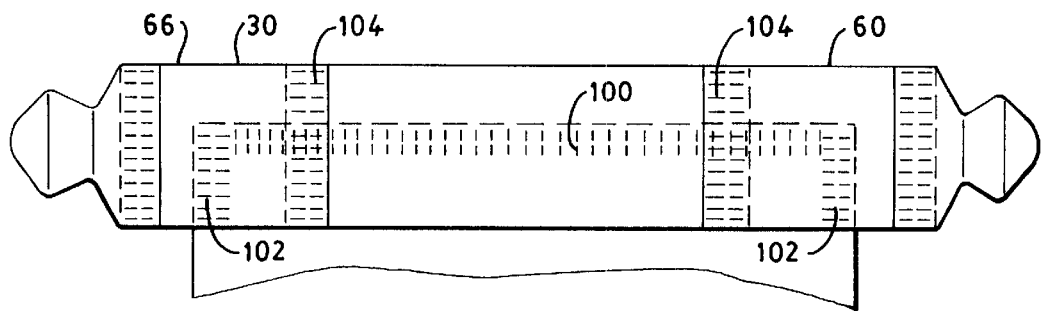
FIG. 5A representatively shows a top plan view of a portion of an absorbent article according to another embodiment of the invention.
Figure 6:
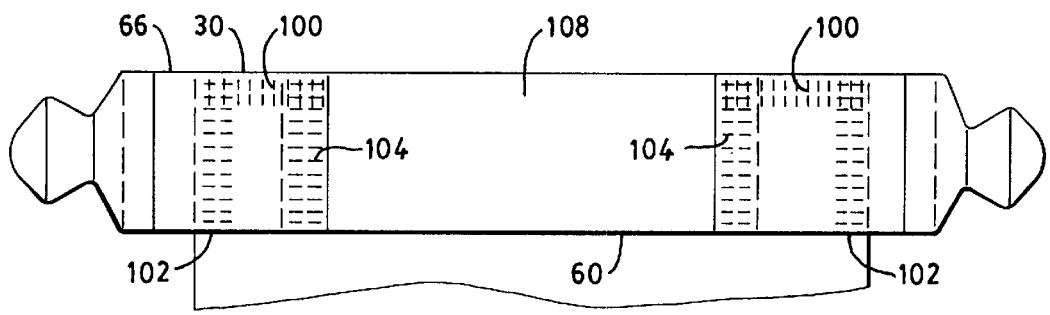
FIG. 6 representatively shows a top plan view of a portion of an absorbent article according to another embodiment of the invention.
Figure 6A:
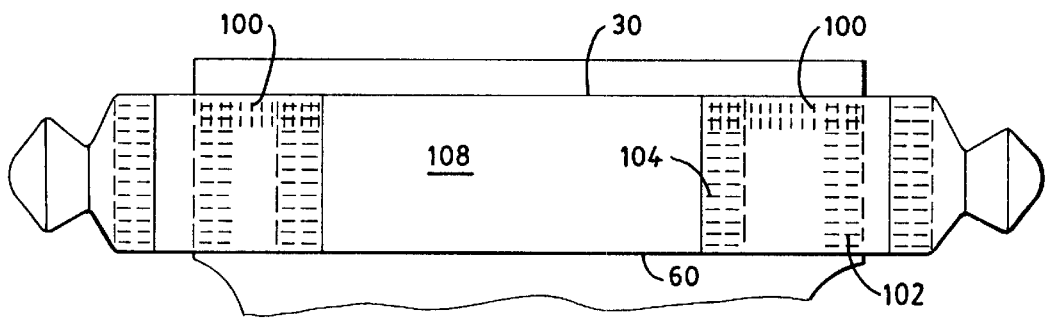
FIG. 6A representatively shows a top plan view of a portion of an absorbent article according to another embodiment of the invention.

Alternatively, the waist edge 66 of the fit panel 60 may be attached directly to the end edge 30 of the absorbent chassis along a lateral attachment zone 100 as illustrated in FIG. 5. If the waist edge 66 of the fit panel 60 extends longitudinally beyond the end edge 30, the end edge 30 of the absorbent chassis may be attached directly to a central area of the fit panel 60 along a lateral attachment zone 100 as illustrated in FIG. 5A. Alternatively, if the end edge 30 of the chassis of the diaper 20 extends longitudinally beyond the waist edge 66 of the fit panel 60, the waist edge 66 of the fit panel 60 may be attached directly to an inward portion of the chassis along a lateral attachment zone 100 as illustrated in FIG. 6A.

It has been further discovered that the fit panel 60 need not be attached to the absorbent chassis of the diaper 20 along it's entire width 64 or length 62. For example, as representatively illustrated in FIGS. 6 and 6A, the fit panel may remain unattached to the topsheet 34 and absorbent chassis of the diaper 20 in an unattached zone 108. The unattached zone 108 may be centered about the longitudinal centerline 74 of the diaper 20 and define a width in the lateral direction 38 of at least about 10 percent and desirably from about 35 to about 65 percent of the width 58 of the absorbent chassis of the diaper 20 in the respective waist section to which the fit panel is attached. In such a configuration, the bridge panel 80 or respective central zone of elasticity 92 may remain unattached to the topsheet 34 of the diaper 20. It has been discovered that such an arrangement allows the absorbent chassis of the diaper 20 to more freely expand and move to better receive and contain body exudates. In a particularly preferred embodiment as representatively illustrated in FIGS. 1 and 2, the fit panel 60 remains substantially unattached to the absorbent chassis between the opposed longitudinal attachment zones 102 located along the side edges 28 of the absorbent chassis. Such a configuration allows additional freedom of movement for the absorbent chassis relative to the fit panel 60 for improved performance.

In another alternative embodiment, the fit panel 60 may be attached to the absorbent chassis in a sleeved configuration. For example, the fit panel 60 may include a slit in the lateral direction 38 located a distance inward from the waist edge 66 of the fit panel 60 towards the second edge 68. In such a sleeved configuration, the fit panel may encircle the end edge of the absorbent chassis and the absorbent chassis may extend at least partially through the slit. The end edge 30 of the absorbent chassis may thus be located either in front of or behind the waist edge 66 of the fit panel 60 as desired.

As representatively illustrated in FIGS. 1–7, the absorbent article of the present invention further includes a pair of fasteners 50 which are attached to the outboard edges 70 and 72 of the fit panel 60. As illustrated, the fasteners 50 may be attached to fastener side panels 52 which may or may not be elastic. The side panels 52 may then be attached to the outboard edges 70 and 72 of the fit panel 60. It has been discovered that the location of the fasteners on the fit panel of the present invention results in a reliable fastening system which maintains the article about the waist of the wearer without causing excessive redmarking or irritation. The size, shape and elastic properties of the fit panel 60 function to distribute the fastening forces across the entire length 62 of the fit panel 60 resulting in such improved fastening when compared to conventional articles which include fastening means which are attached directly to the chassis of the absorbent article. Since the fasteners 50 and fit panel 60 function to maintain the diaper about the wearer, the absorbent chassis of the diaper 20 is free to expand and move relative to the fit panel to receive and contain bodily exudates without adversely affecting the fit and appearance of the diaper 20 on the wearer.

Having thus described the invention in rather full detail, it will be readily apparent to a person of ordinary skill that various changes and modifications can be made without departing from the spirit of the invention. All of such changes and modifications are contemplated as being within the scope of the present invention as defined by the subjoined claims.

We claim:

1. An absorbent article having an absorbent chassis which defines a front waist section, a rear waist section, an intermediate section which interconnects said front and rear waist sections, a pair of longitudinally opposed end edges, and a pair of laterally opposed side edges, said absorbent article further comprising a fit panel attached to said absorbent chassis which defines a waist edge which is superposed adjacent one of said pair of longitudinally opposed end edges of said absorbent chassis, a pair of laterally opposed outboard edges which are located laterally beyond said side edges of said absorbent chassis, respectively, and a second edge which is located longitudinally inward from said one end edge of said absorbent chassis and which remains at least partially unattached to said absorbent chassis wherein at least a portion of a total panel width and length of said fit panel remains unattached to said absorbent chassis between said side edges of said absorbent chassis thereby defining an unattached zone that defines an unattached width which is at least about 10 percent of an entire width of said-absorbent chassis.

2. An absorbent article according to claim 1 wherein said total panel width of said fit panel is at least about 105 percent of said entire width of said absorbent chassis.

3. An absorbent article according to claim 1 wherein said total length of said fit panel extends longitudinally inward from said one end edge towards said intermediate section and is at least about 5 percent of an entire length of said absorbent chassis.

4. An absorbent article according to claim 1 wherein said absorbent article further comprises a pair of fasteners which are connected to said outboard edges of said fit panel.

5. An absorbent article according to claim 1 wherein said unattached width is from about 35 to about 65 percent of said entire width of said absorbent chassis.

6. An absorbent article according to claim 1 wherein said fit panel is attached to said absorbent chassis along a lateral attachment zone which is located a distance of from about 0.5 to about 4.0 centimeters longitudinally inward from said one end edge of said absorbent chassis and wherein said fit panel remains substantially unattached to said absorbent chassis longitudinally outward from said lateral attachment zone.

7. An absorbent article according to claim 6 wherein said absorbent article further comprises a pair of fasteners which are connected to said outboard edges of said fit panel, respectively, and wherein said lateral attachment zone is located along a path extending between said fasteners.

8. An absorbent article according to claim 1 wherein said waist edge of said fit panel extends longitudinally outward from said one end edge of said absorbent chassis.

9. An absorbent article according to claim 1 wherein said fit panel is secured to said absorbent chassis such that said absorbent chassis is gathered from about 3 to about 50 percent when said fit panel is relaxed.

10. An absorbent article according to claim 1 wherein said fit panel is elastomeric.

11. An absorbent article according to claim 10 wherein said elastomeric fit panel defines two zones of elasticity across said total panel width of said fit panel which define different elastic properties.

12. An absorbent article according to claim 11 wherein said elastomeric fit panel comprises a single panel of material and said zones of elasticity are provided by reducing said elastic properties of selected ones of said zones of elasticity of said fit panel.

13. An absorbent article according to claim 11 wherein said elastomeric fit panel comprises two individual panels of material which are connected together to provide said zones of elasticity.

14. An absorbent article according to claim 10 wherein said elastomeric fit panel comprises an elastomeric neck-bonded-laminate material.

15. An absorbent article according to claim 10 wherein said elastomeric fit panel is capable of providing an elongation in a lateral direction of at least about 5 percent when subjected to a tensile force load of about 80 grams in said lateral direction per lineal centimeter of said fit panel measured in a longitudinal direction.

16. An absorbent article according to claim 1 wherein said waist edge of said fit panel extends longitudinally beyond said one end edge of said absorbent chassis.

17. An absorbent article having an absorbent chassis which defines a front waist section, a rear waist section, an intermediate section which interconnects said front and rear waist sections, a pair of longitudinally opposed end edges, and a pair of laterally opposed side edges, said absorbent article further comprising a fit panel which is located in one of said waist sections of said absorbent chassis adjacent one of said end edges of said absorbent chassis and which extends laterally beyond said side edges of said absorbent chassis wherein said fit panel comprises:
  a) a center bridge panel which defines a bridge panel width which is from about 10 to about 90 percent of an entire width of said absorbent chassis, and
  b) a pair of laterally opposed, individual, discrete side panels which are connected to opposed lateral edges of said bridge panel and which are connected to and extend laterally beyond said side edges of said absorbent chassis, respectively.

18. An absorbent article according to claim 17 wherein said fit panel defines a total panel width which is at least about 105 percent of said entire width of said absorbent chassis.

19. An absorbent article according to claim 17 wherein said fit panel defines a waist edge which is superposed adjacent said one end edge of said absorbent chassis, a pair of laterally opposed outboard edges which are located laterally beyond said side edges of said absorbent chassis, respectively, and a second edge which is located longitudinally inward from said one end edge of said absorbent chassis and which remains at least partially unattached to said absorbent chassis.

20. An absorbent article according to claim 19 wherein said absorbent article further comprises a pair of fasteners which are connected to said outboard edges of said fit panel, respectively.

21. An absorbent article according to claim 19 wherein at least a portion of a total panel width of said fit panel remains at least partially unattached to said absorbent chassis between said side edges of said absorbent chassis.

22. An absorbent article according to claim 19 wherein said fit panel is attached to said absorbent chassis along a pair of longitudinal attachment zones located adjacent said side edges of said absorbent chassis, respectively, and wherein said fit panel remains unattached to said absorbent chassis between said longitudinal attachment zones.

23. An absorbent article according to claim 19 wherein said fit panel is attached to said absorbent chassis along a lateral attachment zone which is located a distance of from about 0.5 to about 4.0 centimeters longitudinally inward from said one end edge of said absorbent chassis and wherein said fit panel remains substantially unattached to said absorbent chassis longitudinally outward from said lateral attachment zone.

24. An absorbent article according to claim 17 wherein said bridge panel width of said bridge panel is from about 30 to about 70 percent of said entire width of said absorbent chassis.

25. An absorbent article according to claim 24 wherein said side panels of said fit panel extends laterally inward from said side edges of said absorbent chassis, respectively, to said bridge panel.

26. An absorbent article according to claim 17 wherein at least a portion of said bridge panel width of said bridge panel remains unattached to said absorbent chassis thereby defining an unattached width.

27. An absorbent article according to claim 26 wherein said unattached width is at least about 10 percent of said entire width of said absorbent chassis.

28. An absorbent article according to claim 17 wherein said bridge panel remains substantially unattached to said absorbent chassis.

29. An absorbent article according to claim 17 wherein a portion of said fit panel is elastomeric.

30. An absorbent article according to claim 17 wherein said side panels are elastomeric.

31. An absorbent article according to claim 17 wherein said side panels and said bridge panel are elastomeric.

32. An absorbent article having a front waist section, a rear waist section, and an intermediate section which interconnects said front and rear waist sections, said article further comprising:
  a) a backsheet layer;
  b) a liquid permeable topsheet layer which is connected in superposed relation to said backsheet layer;
  c) an absorbent body which is located between said topsheet layer and said backsheet layer wherein a combination of said backsheet layer, said topsheet layer, and said absorbent body define an absorbent chassis which includes an outer perimeter defined by a pair of longitudinally opposed end edges and a pair of laterally opposed side edges; and d) an elastomeric fit panel which is connected to said topsheet in one of said waist sections of said absorbent article and which defines a waist edge which is superposed adjacent one of said end edges of said absorbent chassis, a pair of laterally opposed outboard edges which are located laterally beyond said side edges, respectively, and said outer perimeter of said absorbent chassis, and a second edge which is located longitudinally inward from said one end edge of said absorbent chassis and which remains at least partially unattached to said absorbent chassis wherein at least a portion of a total panel width and total length of said elastomeric fit panel remains unattached to said topsheet between said side edges of said absorbent chassis thereby defining an unattached zone that defines an unattached width which is at least about 10 percent of an entire width of said absorbent chassis.

33. An absorbent article according to claim 32 wherein said total panel width is at least about 105 percent of said entire width of said absorbent chassis.

34. An absorbent article according to claim 32 wherein said elastomeric fit panel extends laterally beyond each of said side edges of said absorbent chassis a distance of at least about 0.5 centimeters.

35. An absorbent article according to claim 32 wherein said total length of said elastomeric fit panel extends longitudinally inward from said one end edge of said absorbent chassis towards said intermediate section and is at least about 5 percent of an entire length of said absorbent chassis.

36. An absorbent article according to claim 32 wherein said absorbent article further comprises a pair of fasteners which are connected to said outboard edges of said elastomeric fit panel, respectively.

37. An absorbent article according to claim 32 wherein said elastomeric fit panel is attached to said absorbent chassis along a pair of longitudinal attachment zones located adjacent said side edges of said absorbent chassis, respectively, and wherein said elastomeric fit panel remains unattached to said absorbent chassis between said longitudinal attachment zones.

38. An absorbent article according to claim 32, wherein said elastomeric fit panel is attached to said topsheet of said absorbent article along a lateral attachment zone which is located a distance of from about 0.5 to about 4.0 centimeters longitudinally inward from said one end edge of said absorbent chassis and wherein said elastomeric fit panel which extends longitudinally outward from said lateral attachment zone remains substantially unattached to said topsheet of said absorbent article.

39. An absorbent article according to claim 32 wherein said elastomeric fit panel is secured to said absorbent chassis such that said absorbent chassis is gathered from about 3 to 50 percent when said elastomeric fit panel is relaxed.

40. An absorbent article according to claim 32 wherein said elastomeric fit panel defines two zones of elasticity across said total panel width of said fit panel each of which defines a different moduli of elasticity.

41. An absorbent article according to claim 32 wherein said elastomeric fit panel comprises:

a) a bridge panel, and b) a pair of individual, discrete side panels which are connected to opposed lateral edges of said bridge panel, respectively, and which are connected to and extend laterally beyond said side edges of said absorbent chassis, respectively.

42. An absorbent article according to claim 41 wherein said absorbent article further comprises a pair of fasteners which are connected to laterally opposed outboard edges of said side panels of said elastomeric fit panel, respectively.

43. An absorbent article according to claim 41 wherein said bridge panel defines a total bridge panel width which is at least about 10 percent of said entire width of said absorbent chassis.

44. An absorbent article according to claim 43 wherein said side panels of said elastomeric fit panel extends laterally inward from said side edges of said absorbent chassis, respectively, to said bridge panel.

45. An absorbent article according to claim 41 wherein at least a portion of a total bridge panel width of said bridge panel remains unattached to said absorbent chassis to provide said unattached width.

46. An absorbent article according to claim 41 wherein said bridge panel remains substantially unattached to said absorbent chassis to provide said unattached width.

47. An absorbent article according to claim 41 wherein said bridge panel and at least a portion of said side panels between said bridge panel and said side edges of said absorbent chassis respectively remain substantially unattached to said absorbent chassis.

48. An absorbent article according to claim 41 wherein each of said side panels are configured to elongate a greater percentage than said bridge panel when a force in a lateral direction is exerted on said fit panel.

* * * * *